US008989836B2

(12) United States Patent
Machon et al.

(10) Patent No.: US 8,989,836 B2
(45) Date of Patent: Mar. 24, 2015

(54) ELECTRODE ARRAY AND METHOD OF PLACEMENT

(71) Applicant: Brainscope Company, Inc., Bethesda, MD (US)

(72) Inventors: Lukasz W. Machon, Darnestown, MD (US); Neil S. Rothman, Baltimore, MD (US)

(73) Assignee: Brainscope Company, Inc., Bethesda, MD (US)

( * ) Notice: Subject to any disclaimer, the term of this patent is extended or adjusted under 35 U.S.C. 154(b) by 152 days.

(21) Appl. No.: 13/790,149

(22) Filed: Mar. 8, 2013

(65) Prior Publication Data

US 2014/0257073 A1    Sep. 11, 2014

(51) Int. Cl.
*A61B 5/0478*   (2006.01)
*A61B 5/00*     (2006.01)

(52) U.S. Cl.
CPC ............. *A61B 5/6803* (2013.01); *A61B 5/0478* (2013.01); *A61B 5/6814* (2013.01); *A61B 5/684* (2013.01); *A61B 2562/164* (2013.01)
USPC ............................. 600/383; 600/393; 600/544

(58) Field of Classification Search
CPC .. A61B 5/0478; A61B 5/6803; A61B 5/6814; A61B 5/6815
USPC ................................. 600/383, 393, 544, 545
See application file for complete search history.

(56) References Cited

U.S. PATENT DOCUMENTS

| | | | |
|---|---|---|---|
| D560,809 S | 1/2008 | Causevic et al. | |
| D603,051 S | 10/2009 | Causevic et al. | |
| 7,720,530 B2 | 5/2010 | Causevic | |
| 7,904,144 B2 | 3/2011 | Causevic et al. | |
| D641,886 S | 7/2011 | Causevic et al. | |
| D647,208 S | 10/2011 | Rothman et al. | |
| 8,364,254 B2 | 1/2013 | Jacquin et al. | |
| 8,391,948 B2 * | 3/2013 | Causevic et al. | 600/383 |
| 8,473,024 B2 * | 6/2013 | Causevic et al. | 600/383 |
| 8,821,397 B2 * | 9/2014 | Al-Ali et al. | 600/301 |

(Continued)

FOREIGN PATENT DOCUMENTS

WO    WO 2009/100654 A1    8/2009

OTHER PUBLICATIONS http://www.masimo.com/sedline/products.htm [Accessed Apr. 15. 2012].

(Continued)

*Primary Examiner* — Lee S Cohen
(74) *Attorney, Agent, or Firm* — Finnegan, Henderson, Farabow, Garrett & Dunner, LLP

(57) ABSTRACT

A headset for detecting brain electrical activity may include a flexible substrate having first and second ends each configured to engage an ear of a subject and dimensioned to fit across the forehead of a subject. The headset may also include a plurality of electrodes disposed on the substrate and configured to contact the subject when the headset is positioned on the subject. First and second electrodes may contact top center and lower center regions of the forehead, respectively, third and fourth electrodes may contact front right and front left regions of the forehead, respectively, fifth and sixth electrodes may contact right side and left side regions of the forehead, respectively, and electrodes included within the securing devices may contact the ear regions. The third and fourth electrodes may be moveable in at least a vertical direction relative to the other electrodes.

10 Claims, 11 Drawing Sheets

(56) References Cited

U.S. PATENT DOCUMENTS

2007/0032737 A1*  2/2007  Causevic et al. ............. 600/544
2009/0018427 A1   1/2009  Causevic et al.
2010/0041962 A1   2/2010  Causevic et al.
2011/0144520 A1   6/2011  Causevic et al.
2011/0282232 A1  11/2011  Pradeep et al.
2012/0065536 A1   3/2012  Causevic et al.
2013/0331660 A1* 12/2013  Al-Ali et al. ................. 600/301

OTHER PUBLICATIONS http://www.hydrodot.net/Products/statnet.html [Accessed Apr. 15, 2012].

PCT International Search Report and PCT Written Opinion of the International Searching Authority for corresponding PCT application PCT/US2014/015721, mailed Jun. 25, 2014, (12 pages total).

* cited by examiner

ELECTRODE ARRAY AND METHOD OF PLACEMENT

FIELD OF THE DISCLOSURE

Embodiments of the present disclosure relate to, among other things, medical devices and, in particular, to an electrode array for sensing brain electrical activity and a method of placing electrodes.

BACKGROUND OF THE DISCLOSURE

The central nervous system (CNS), and the brain in particular, perform some of the most complex and essential processes in the human body. Surprisingly, contemporary health care often lacks the tools to objectively and effectively assess brain function at the point-of-care. A person's mental and neurological status is typically assessed using an interview and a subjective physical exam. Clinical laboratories may not have the capacity to effectively assess brain function or pathology, and may be largely limited to the identification of poisons, toxins, drugs, or other foreign substances that may have impacted the central nervous system (CNS).

Brain imaging technologies, such as computed tomography imaging (CT), magnetic resonance imaging (MRI), positron emission tomography (PET), and single photon emission computerized tomography (SPECT) may be used to visualize the structure of the brain. Yet these anatomical tests may reveal little information about brain function. For example, intoxication, concussion, active seizure, metabolic encephalopathy, infections, diabetic coma, and numerous other conditions may show no abnormality on a CT scan. Even a stroke or a traumatic brain injury (TBI) may not be immediately visible in an imaging test, even when a person has clearly observable abnormal brain function. CT and MRI may only detect a change in brain function after the morphology or structure of the brain has changed. Thus, in some cases, it may take hours or days after the onset of a condition before severe neurological pathology is visible on the CT or MRI.

Such limitations may be especially significant after trauma, because the brain may require immediate attention to avoid further deterioration. For example, diffuse axonal injury (DAI), related to shearing of nerve fibers and present in many concussive brain injury cases, may remain invisible on most routine structural images. If undetected at an early stage, swelling or edema from DAI may lead to coma and death.

Functional MRI (fMRI), a recent improvement over MRI, provides relative images of the concentration of oxygenated hemoglobin in various parts of the brain. While the concentration of oxygenated hemoglobin may be a useful indication of the metabolic function of specific brain regions, it may provide limited or no information about the underlying brain function, i.e., the processing of information by the brain, which is electrochemical in nature. Another recent improvement, diffusion MRI (dMRI) maps the diffusion process of molecules, such as water, in the brain and may provide details about tissue architecture. One type of dMRI, diffusion tensor imaging (DTI), has been used successfully to indicate abnormalities in white matter fiber structure and to provide models of brain connectivity. DTI may provide a viable imaging tool for the detection of DAI, but such imaging again focuses on anatomical information rather than brain function.

All of the brain's activity, whether sensory, cognitive, emotional, autonomic, or motor function, is electrical in nature. Through a series of electrochemical reactions, mediated by molecules called neurotransmitters, electrical potentials (voltages) are generated and transmitted throughout the brain, traveling continuously between and among a myriad of neurons. This activity establishes the basic electrical signature of the electroencephalogram (EEG) and creates identifiable frequencies that may have a basis in anatomic structure and function. Understanding these basic rhythms and their significance may make it possible to characterize the electrical brain signals as being within or beyond normal limits. At this basic level, the electrical signals may serve as a signature for both normal and abnormal brain function. Just as an abnormal electrocardiogram (ECG) pattern is a strong indication of a particular heart pathology, an abnormal brain wave pattern may be a strong indication of a particular brain pathology. Additionally, the electrical activity of the brain may be affected closer to the onset of a condition, before any structural changes have occurred.

Even though EEG-based neurometric technology is generally accepted today in neurodiagnostics, its application in the clinical environment is notably limited. Using standard EEG technology, it may take a skilled technician 1 to 4 hours to administer a test. A neurologist must then interpret the data and make a clinical assessment.

Furthermore, some equipment used for recording EEG data may be too bulky or may be inappropriate for certain situations. For example, standard EEG equipment may require a technician to individually apply 19 or more electrodes onto the scalp of a subject. Each electrode must be placed directly onto the scalp of the subject (often with a conductive gel or paste) in the correct location on the subject's head. Applying the electrodes, each with its own lead wire, may be tedious and time consuming, taking thirty minutes or longer to complete. Application may be further complicated because the electrode wires may easily become tangled and may interfere with other operations. The lack of portability of EEG technology may make it infeasible for point-of-care applications.

To make EEG technology easier to apply to a subject, some products have incorporated electrodes into nets or caps that may be placed on the subject's head. Once in position, a technician can then individually place and attach each electrode to the scalp. While this may decrease preparation time, it still requires a technician to place each electrode.

Other products have tried to eliminate the need to individually place each electrode by allowing an administrator to apply all of the electrodes at once to a subject. Such products fix the relative positioning of electrodes in a headset, which may then be fitted to the subject. Thus, by incorporating all of the electrodes into a headset and fixing their relative location, placement of the electrodes is complete once the headset is positioned on the subject, substantially reducing the preparation time. Such technology has worked to some extent for anesthesiologists in sedation applications, for example, to detect whether a person's EEG readings indicate proper sedation based on pre-sedation and post-sedation readings of that same person. Yet, grouping the electrodes in this manner has proven surprisingly inadequate and unreliable for capturing EEG readings capable of discriminating between levels of normal versus abnormal brain activity for a given person relative to a population.

Without a quick and reliable way of placing electrodes for EEG readings, current EEG equipment and electrode arrays may not be practical for the emergency room (ER), operating room (OR), intensive care unit (ICU), first response situations, sporting events, the battlefield, or other point-of-care settings and situations. Thus, there is an immediate need for a portable brain state assessment technology to provide rapid neurological evaluation and treatment guidance for subjects with acute brain injury or disease, so as to prevent further brain damage and disability. This in turn may help medical personnel select an immediate course of action, prioritize people for imaging, and determine whether immediate referral to a neurologist or neurosurgeon is required.

Embodiments of the disclosure described herein may overcome some disadvantages of the prior art.

SUMMARY OF THE DISCLOSURE

Embodiments of the present disclosure relate to medical devices, such as the placement of electrodes on a subject for sensing brain electrical activity. Various embodiments of the disclosure may include one or more of the following aspects.

In accordance with one embodiment, a headset for detecting brain electrical activity may include a flexible substrate dimensioned to fit a forehead of a subject. The substrate may have a first end and a second end each configured to engage an ear of a subject to position the substrate across the forehead. The substrate may include at least one expansible region permitting a distance between the first and second ends to selectably vary. The headset may also include a plurality of electrodes disposed on the substrate so that the electrodes contact the subject when the headset is positioned on the subject. A first electrode may be configured to contact a top center region of the forehead, a second electrode may be configured to contact a lower center region of the forehead, a third electrode may be configured to contact a front right region of the forehead, a fourth electrode may be configured to contact a front left region of the forehead, a fifth electrode may be configured to contact a right side region of the forehead, and a sixth electrode may be configured to contact a left side region of the forehead. One electrode may be included within each securing device and configured to contact an ear region of the subject when the headset is positioned on the subject, and at least the third and fourth electrodes may be moveable in at least a vertical direction relative to the other electrodes when the headset is positioned on the subject. The headset may also include flexible circuitry in the substrate operably coupled to the electrodes.

Various embodiments of the headset may include one or more of the following features: at least one of the plurality of electrodes may be grounded; at least the third and fourth electrodes may each include a distance indication gauge; the distance indication gauge may include a tab with a first end connected to the electrode and a second free end extending from the electrode; the distance from the second end of the distance indication gauge to a center of the electrode may substantially equal the distance that the electrode is located from an anatomical feature of the subject; the anatomical feature may be an eyebrow; and the at least one expansible region may include a flexure or corrugation in the substrate.

In accordance with another embodiment, a method of applying a headset may include: applying a first sensor to a left ear region, applying a second sensor to a right ear region, applying a third sensor to an upper center region of the forehead, applying a fourth sensor to the forehead, applying a fifth sensor to a left frontal region of the forehead, applying a sixth sensor to a right frontal region of the forehead, applying a seventh sensor to a left side region of a forehead, applying an eighth sensor to a right side region of the forehead, wherein the headset includes a flexible substrate dimensioned to fit the forehead of the subject having a first end and a second end, wherein the first end and the second end each includes a securing device configured to engage an ear of the subject to position the flexible substrate across the forehead, wherein the flexible substrate includes at least one distance gauge configured to indicate the distance from an anatomical region of the subject from which to apply at least one sensor, and wherein the headset includes a connector region, and the method further includes connecting the connector region to a processor.

Various embodiments of the method may include one or more of the following features: the connecting may include wirelessly or physically connecting the connector region to the processor; the processor may be housed in a portable handheld device and configured to receive data from at least one sensor; the method may further include conducting an impedance check, wherein the portable handheld device transmits at least one signal to each sensor and measures a resulting current from each sensor to identify an impedance value for each sensor; the portable handheld device may include a display screen for displaying the impedance value for each sensor and the method may further include comparing the identified impedance value for each sensor to a predetermined impedance range to determine whether the impedance value falls within the range and adjusting any sensor that has an impedance value that falls outside of the range to cause the impedance value for that sensor to fall within the range; the substrate may include at least an expansible region permitting a distance between the first end and the second end to selectably vary; the fourth sensor may be applied to a lower center region of the forehead of the subject and the fourth sensor may be grounded; the anatomical region of the subject may be an eyebrow; a first distance gauge may include a tab extending from a lower region of the fifth sensor and a second distance gauge may include a tab extending from a lower region of the sixth sensor; applying the fifth sensor and applying the sixth sensor may include adjusting the respective tabs so that a distal region of the tabs sits directly above the eyebrows without touching the eyebrows; at least one sensor may be removable; applying the third sensor may include placing the third sensor below a hairline of the subject; the anatomical region may be a nasion of the subject; and the distance gauge may include an elongated section extending from the fourth sensor and applying the fourth sensor may include positioning the distance gauge so that a distal portion of the distance gauge is directly above the nasion.

In accordance with another embodiment, a headset for detecting brain electrical activity may include: a flexible substrate dimensioned to fit a forehead of a human subject having a first end and a second end, wherein the first end and the second end each includes a securing device configured to engage an ear of the subject to position the flexible substrate across the forehead, and wherein the flexible substrate includes at least one expansible region permitting a distance between the first end and the second end to selectably vary; a first sensor disposed on the flexible substrate and configured to contact an upper center region of the forehead when the headset is positioned on the subject; a second sensor disposed on the flexible substrate and configured to contact a lower center region of the forehead when the headset is positioned on the subject; a third sensor disposed on the flexible substrate and configured to contact a left frontal region of the forehead when the headset is positioned on the subject, wherein the headset is adjustable such that the position of the third sensor is movable relative to the position of the first sensor; a fourth sensor disposed on the flexible substrate and configured to contact a right frontal region of the forehead when the headset is positioned on the subject, wherein the headset is adjustable such that the position of the fourth sensor is movable relative to the position of the first sensor; a fifth sensor disposed on the flexible substrate and configured to contact a left side region of the forehead when the headset is positioned on the subject;

a sixth sensor disposed on the flexible substrate and configured to contact a right side region of the forehead when the headset is positioned on the subject; a seventh sensor disposed on the first end of the flexible substrate and configured to contact a left ear region of the subject when the headset is positioned on the subject; and an eighth sensor disposed on the second end of the flexible substrate and configured to contact a right ear region of the subject when the headset is positioned on the subject, wherein the second sensor, the third sensor, and the fourth sensor each includes an elongated portion having a first end connected to the sensor and a free end extending from the sensor.

Further, a method of applying this headset may include: positioning the free end of the elongated portion of the second sensor at a nasion region of the subject to align the second sensor and the first sensor on the forehead; adjusting the location of the first sensor so that the first sensor is located on the forehead below a hairline of a subject; attaching the first sensor and the second sensor to the forehead of the subject; engaging the first end with a first ear region of the subject; engaging the second end with a second ear region of the subject; attaching the seventh sensor to the first ear region and attaching the eighth sensor to the second ear region; positioning the free end of the elongated portion of the third sensor directly above a first eyebrow of the subject so that the free end does not touch the first eyebrow and attaching the third sensor to the forehead of the subject; positioning the free end of the elongated portion of the fourth sensor directly above a second eyebrow of the subject so that the free end does not touch the second eyebrow and attaching the fourth sensor to the forehead of the subject; attaching the fifth sensor to the forehead of the subject; and attaching the sixth sensor to the forehead of the subject.

BRIEF DESCRIPTION OF THE DRAWINGS

The accompanying drawings illustrate certain embodiments of the present disclosure, and together with the description, serve to explain principles of the present disclosure.

DETAILED DESCRIPTION OF EMBODIMENTS

Reference will now be made in detail to the embodiments of the present disclosure described below and illustrated in the accompanying drawings. Wherever possible, the same reference numbers will be used throughout the drawings to refer to same or like parts.

While the present disclosure is described herein with reference to illustrative embodiments for particular applications, it should be understood that the disclosure is not limited thereto. Those having ordinary skill in the art and access to the teachings provided herein will recognize additional modifications, applications, embodiments, and substitutions of equivalents all fall within the scope of the invention. Accordingly, the disclosure is not to be considered as limited by the foregoing or following descriptions.

Other features and advantages and potential uses of the present disclosure will become apparent to someone skilled in the art from the following description of the disclosure, which refers to the accompanying drawings.

Figure 1:
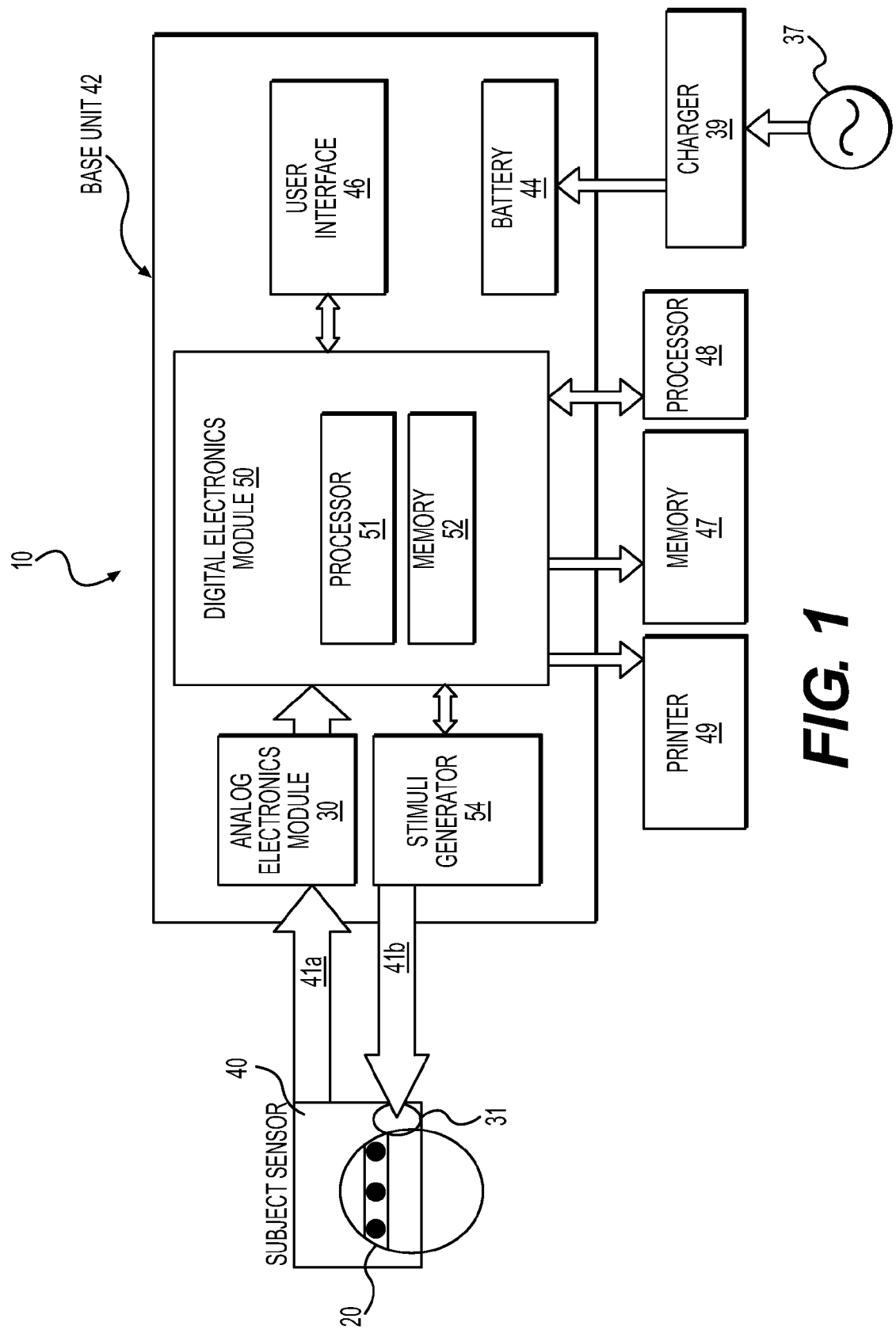
FIG. 1 depicts an exemplary brain assessment system, in accordance with an embodiment of the present disclosure.

In an exemplary embodiment, data corresponding to electrical brain activity may be used to detect neurological injury and/or disease in subjects. FIG. 1 depicts one embodiment of a neuro-assessment apparatus 10 for acquiring and processing electrical brain signals and evaluating a subject's neurological condition. In some embodiments, neuro-assessment apparatus 10 may be implemented as a portable device for point-of-care applications. Apparatus 10 may include a base unit 42, which may be configured either as a handheld unit or as larger, stationary unit. Base unit 42 may be capable of storing, processing, or further transmitting data corresponding to electrical brain activity. For example, base unit 42 may include an analog electronics module 30 and a digital electronics module 50 for receiving and converting EEG signals, a processor 51, a memory 52, a user interface 46 for allowing user input and for outputting data to a user, and a rechargeable and/or replaceable battery 44 for powering apparatus 10. If rechargeable, battery 44 may interface with a charger 39, which in turn may be connectable to an AC power source 37, which may also include appropriate filtering of powerline noise components that could impact signal quality. Further, base 42 may be configured to transmit and/or receive data from any number of suitable components external to apparatus 10, e.g., a printer 49, an external memory 47, or an external processor 48. Memory 47 and/or processor 48 may be included in the same component or in different components, e.g., a computer, a smartphone, a larger database system, a patient monitoring system, etc. Further, base 42 may be operably coupled to these external components either through a hard connection or wirelessly.

Apparatus 10 may also include a subject sensor 40 operably coupled to base unit 42, either by a hard connection or wirelessly. Subject sensor 40 may be configured to detect EEG signals from the subject and transmit this data to base 42, as indicated by arrow 41a. In some embodiments, subject sensor 40 may include an electrode array 20 with one or more disposable neurological sensors, such as electrodes, configured to attach to a subject's head for acquiring electrical brain signals. The electrodes may be configured for sensing spontaneous electrical brain activity and/or evoked potentials generated in response to applied stimuli (e.g. auditory, visual, tactile, etc.), as depicted by optional stimuli generator 54 in base 42, stimulus delivery device 31 either incorporated into or separate from subject sensor 40, and arrow 41b relaying signals between the two.

In one embodiment, array 20 may include 8 electrodes, for example, five active channels and three reference channels. Array 20 may include anterior (frontal) electrodes Fp1, Fp2, F7, F8, AFz (also referred to as Fz') and FPz (ground electrode) configured to attach to a subject's forehead, and electrodes A1 and A2 configured to attach to the front or back side of the ear lobes, or on the mastoids, roughly in accordance with the International 10/20 electrode placement system (with the exception of AFz), as is shown in FIG. 2A.

While the International 10/20 system typically requires at least 19 electrodes placed at intervals across a subject's scalp, reducing the number of electrodes in array 20 may allow array 20 to be positioned on a subject's forehead, thereby eliminating the need to place electrodes over the subject's hair. This may reduce any conduction problems caused by hair and eliminate the need for hair removal. Apparatus 10 may be configured to compensate for the reduced number of electrodes in array 20 by employing signal processing algorithms capable of accommodating for the missing electrodes. Such processing may be performed by processor 51 in base unit 42 or by external processor 48. Although not shown, a processor may be placed on array 20 itself, facilitating data gathering and transmission, or the data processing described herein. Adapting apparatus 10 to work with array 20 having fewer electrodes may allow for quicker placement of the electrodes on a subject, which may in turn facilitate efficient subject monitoring and point-of-care use.

Figure 2A:
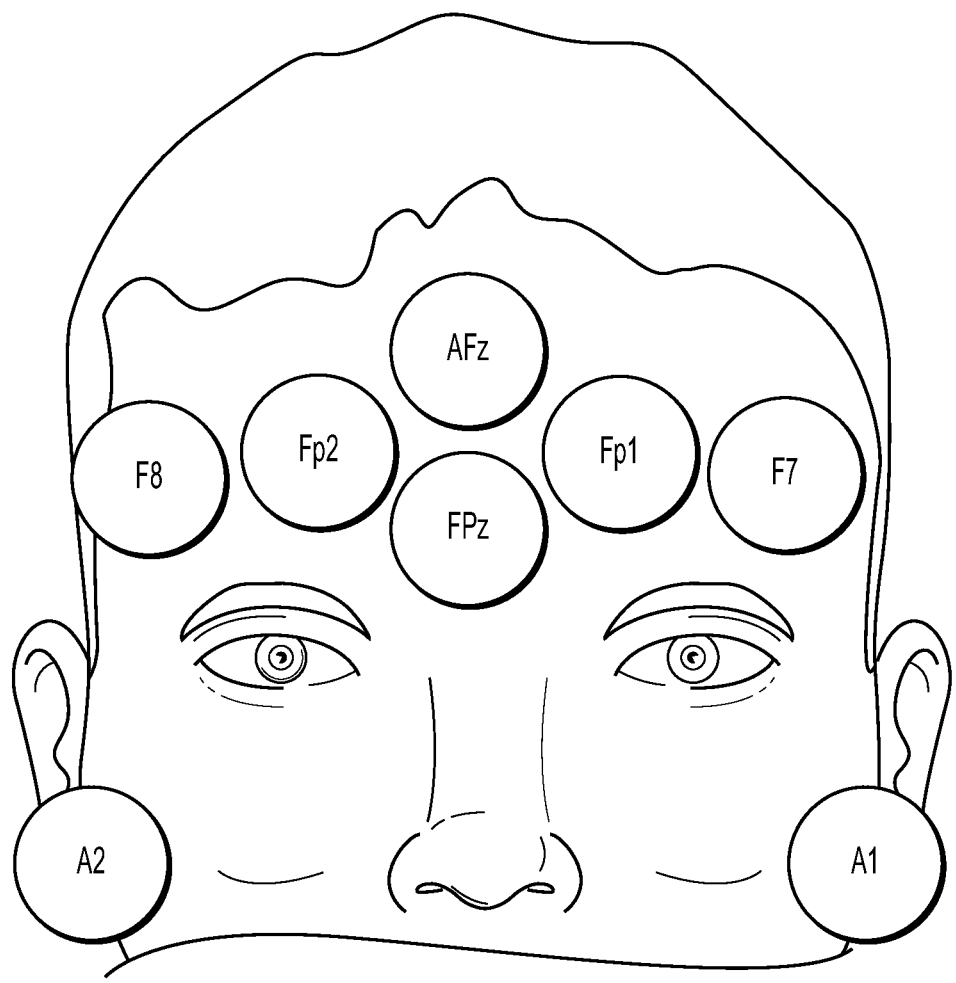
FIG. 2A depicts an exemplary arrangement of sensors, in accordance with an embodiment of the present disclosure.
Figure 2B:
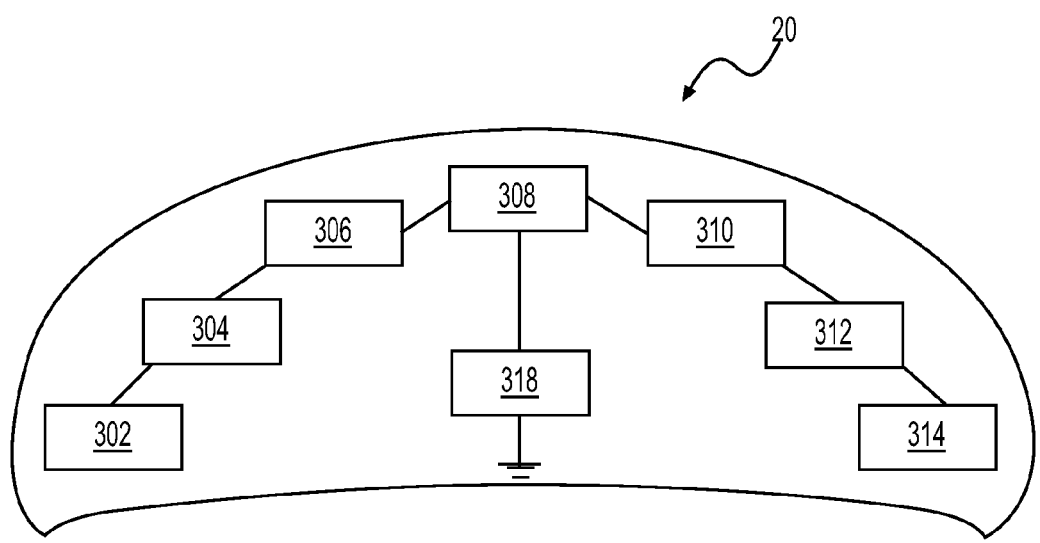
FIG. 2B depicts an exemplary array that may be used with the brain assessment system of FIG. 1.

In accordance with the embodiments depicted in FIGS. 2A and 2B, electrodes Fp1, Fp2, F7, F8, AFz, FPz, A1, and A2, as known from the International 10/20 system, may be placed on the right ear lobe at position 302, on the far right of the forehead at position 304, on the near right of the forehead at position 306, on the center top of the forehead at position 308, on the near left of the forehead at position 310, on the far left of the forehead at position 312, and on the left ear lobe at position 314. Additionally, in an illustrative embodiment, a grounded electrode may be placed on the center of the forehead at position 318.

Though a general desired arrangement of electrodes on the forehead may be known, achieving consistent placement of electrodes across subjects in locations capable of generating usable signals from each electrode has proven very difficult. Individually placing, testing, and adjusting each electrode on a subject using free electrodes may yield the best EEG signals, but individual placement requires more time and a trained technician, as discussed above. This would negate the ease-of-use and portability requirements for a point-of-care embodiment of apparatus 10. Prior art "one-size-fits-all" headsets were created to enable rapid and repeated placement of electrodes on a subject. Electrode nets were designed that adjust in proportion to the size of a subject's head. Thus, though the relative location of the electrodes to one another was not fixed, the electrodes were automatically placed according to the characteristics of the net structure, e.g., the rigidity or elasticity of the net, as it conformed to the subject's head. Such nets did not allow for adjustment of the electrodes once the nets were fitted in place. In addition, headsets were produced that fixed the location of the electrodes relative to each other within the headset, so that when the headset was applied to the subject, the headset dictated the arrangement of the electrodes on the subject's head. These prior art headsets were configured to fit on each subject in substantially the same orientation in an attempt to minimize the risk that an untrained user would not achieve consistent placement of the electrodes. By fixing the location of the electrodes relative to each other, affixing the headset as a unitary whole to the subject essentially simultaneously completed placement of the electrodes, because the headset substrate substantially determined the relative arrangement of the electrodes within it. Thus, the headset itself almost completely dictated the placement of the electrodes rather than the user, notwithstanding differences in facial morphology between subjects.

This fixed-electrode design may generate usable EEG signals in some contexts. For example, headsets with fixed electrode placement have in some instances been used to measure the sedation level of subjects undergoing anesthesia. In this context, the fixed electrode headset may generate EEG signals that are usable to compare and distinguish between a subject's alert levels of electrical brain activity and electrical brain activity indicative of various levels of sedation within that subject. Surprisingly, however, headsets that uniformly fix the placement of electrodes may produce insufficient EEG signals that are incapable of reliably comparing and distinguishing between levels of normal versus abnormal electrical brain activity for an individual subject relative to a population. While not being bound to the theory, this may occur because changes in EEG signals may be more substantial when anesthetizing a subject, but the changes in EEG indicative of brain abnormalities in a subject may be more subtle. Thus, the adverse consequences of fixed-headset designs may be more apparent in more subtle applications, rendering the fixed headsets unusable.

Although fixed-electrode headsets may ensure the 'correct' relative positioning of electrodes as defined by the headset, the subject EEG readings provided by these electrodes surprisingly are not actually usable for all applications, which may be unexpected to one of skill in the art. Further, adjusting the headset to accommodate the anatomy of different subjects (e.g., moving the headset to avoid the hair line or other anatomical feature) or offering different sizes of fixed electrode headsets (e.g., youth or adult) did not appear to achieve more usable EEG readings. Thus, the problem of providing an easy-to-apply set of electrodes for a point-of-care neuro-assessment apparatus remained, and a need persisted for a headset and method for accurately and efficiently applying electrodes to a subject.

Figure 3:
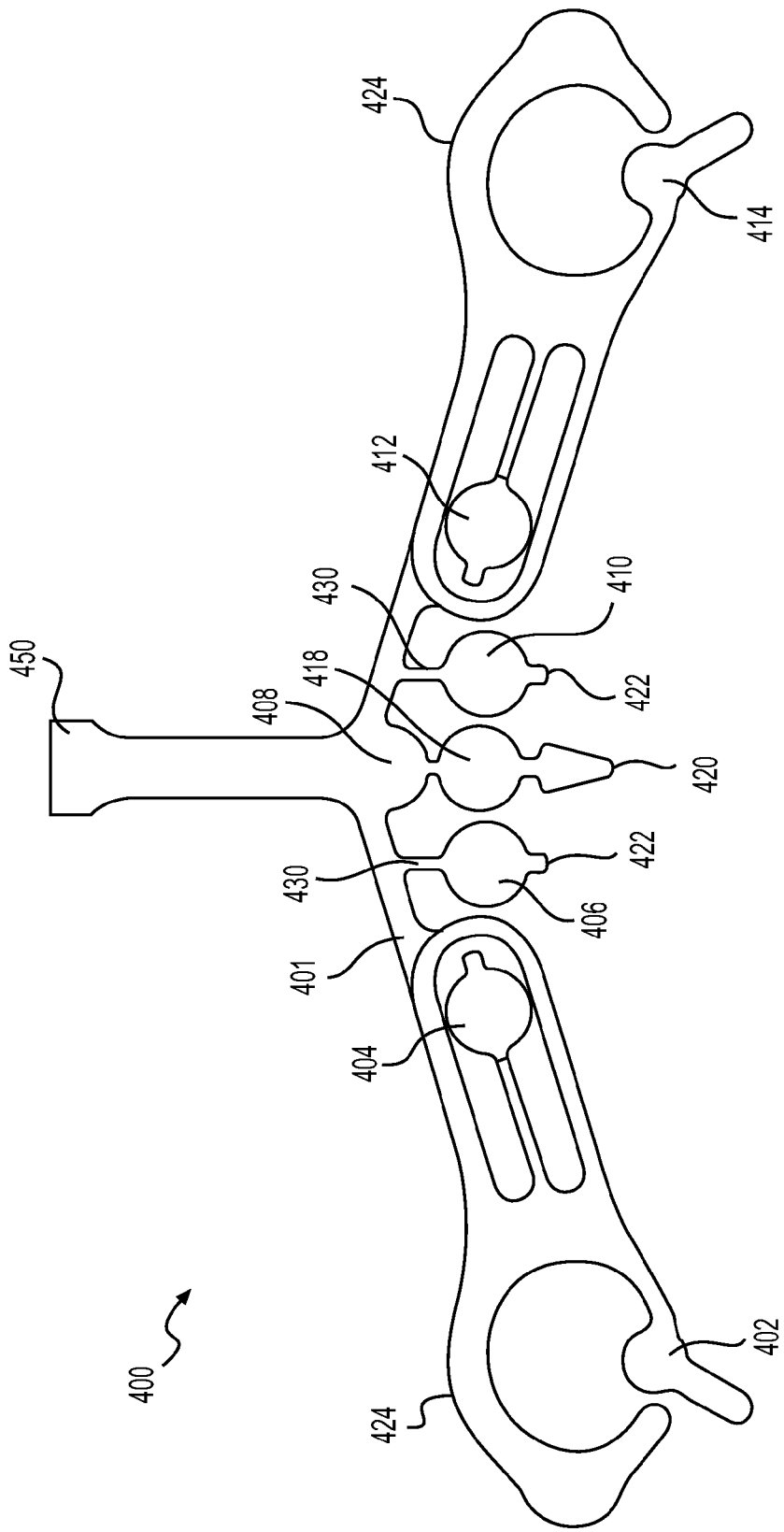
FIG. 3 depicts an exemplary array, in accordance with an embodiment of the present disclosure.

According to an embodiment of the present disclosure, FIG. 3 depicts an electrode array 400 configured to solve at least some of the above problems. Array 400 includes a substrate 401; right and left ear lobe electrodes 402, 414; far right and far left forehead electrodes 404, 412; near right and near left forehead electrodes 406, 410; center top forehead electrode 408; and grounded center electrode 418. Though grounded electrode 418 is shown in the lower center of array 400, electrode 418 may be located in any suitable position on array 400. In some embodiments, including the one shown in FIG. 3, array 400 may include two bilateral "branches" (e.g., extensions left and right of a centerline corresponding approximately with the nose), each configured to extend laterally along respective approximate halves of a subject's forehead region. The electrodes may be arranged along the branching portions of array 400. In the embodiments of FIGS. 3-5, the electrodes may connect to the branching portions of array 400 via, e.g., connector regions 430. While some of the electrodes may be attached directly to neighboring electrodes in array 400 (e.g., central electrode 408 and ground electrode 418), some of the electrodes may be independently connected to each branch of array 400 and, for example, may extend from the branching portions of headset 400 via separate, individual connections. The array 400 depicted in FIG. 3 is bilaterally symmetrical, with the connector region 450 aligning approximately with the nasal centerline, but this needn't be the case.

Array 400 may be sized and shaped to conform to a subject's forehead. Array 400 may be configured to extend from an ear region of the subject and across the forehead, and may include securing devices 424, such as ear loops, to fit over a subject's ears and hold array 400 in place. Further, ear loops 424 may position electrodes 402 and 414 on a subject's ear lobes. Though ear loops 424 are depicted as maintaining array 400 in place, any suitable mechanism, for example, bands, straps, adhesives, snaps, Velcro® or clamps, either completely or partially encircling or affixing array 400 to the head, may be used in addition to or instead of ear loops 424 to maintain array 400 in place. Further, although a branching configuration is described in the exemplary embodiment, array 400 may have any suitable shape, size and configuration.

The electrodes may be incorporated into array 400 on the side of array 400 configured for contacting the subject. The portion of the electrodes configured for subject contact may be exposed and may either lie flush with array 400 or may slightly recess into or project from array 400. To protect the electrodes prior to use, the exposed surfaces may be covered, for example with a removable cover or covers, until array 400 is applied to a subject. Further, array 400 may also include a wet or dry gel over the electrodes and protected by the cover to aid in electrode placement. Alternatively, gel may be applied to the subject or to the electrode directly before use. In some embodiments, the electrodes (with the possible exception of electrodes 402, 414) may be spatially arranged in array 400 to reflect the approximate 10% and 20% distance away from a center nasion tab 420 (discussed further below), according to the International 10/20 system, as estimated for the head size of an average subject.

Array 400 may include circuitry embedded into or printed, coated, etched, deposited or bonded onto array 400 to operate in conjunction with the electrodes. The circuitry may be composed of any suitable electrically conductive material, such as, for example, copper, silver, silver-chloride, gold, tin, or any combination of materials known in the art. The circuitry may electrically connect each electrode, either individually or jointly, to connector region 450 and/or to a transmitter capable of relaying the detected electrical brain activity data from the electrodes to base 42 or external processor 48. Array 400 may include a base interface region 450 configured to connect with base 42, either wirelessly or through a hard connection. Though interface region 450 is depicted at the center of array 400 and array 400 is depicted as symmetrical, base interface region may be any suitable size and shape and may be positioned anywhere on array 400. Further, in wireless embodiments, base interface region may include a transmitter for transmitting data, or may be entirely missing from array 400.

Unlike previous electrode headsets, array 400 may be configured to achieve accurate application of electrodes by an untrained person while generating usable EEG readings for assessing normal versus abnormal brain function. Array 400 will be further described below in reference to the application of array 400 to the subject.

Figure 4A:
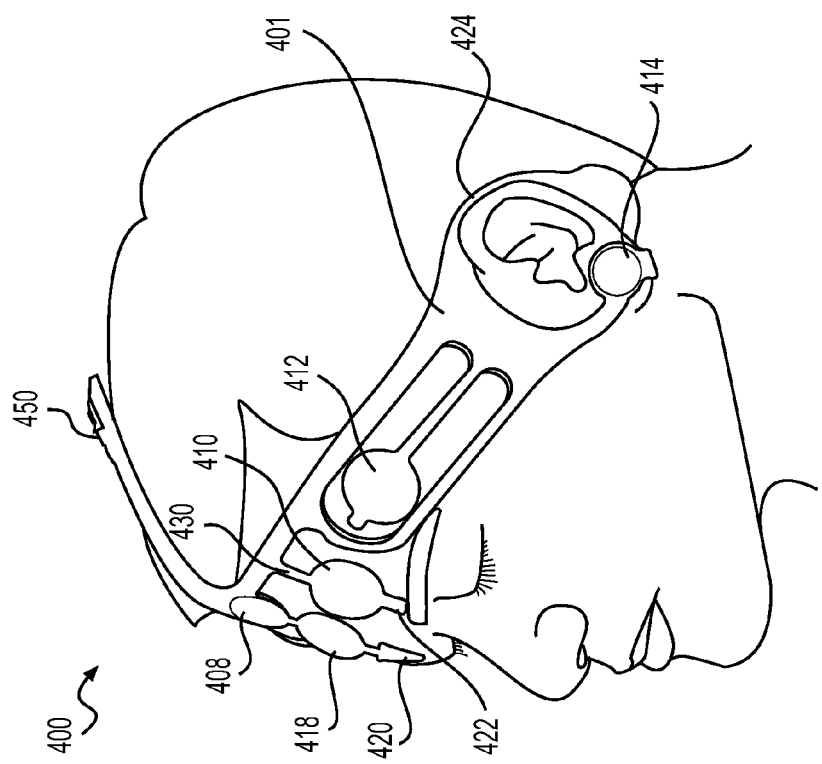
FIG. 4A depicts a side view of the exemplary array of FIG. 3 when fitted on a subject, in accordance with an embodiment of the present disclosure.
Figure 4B:
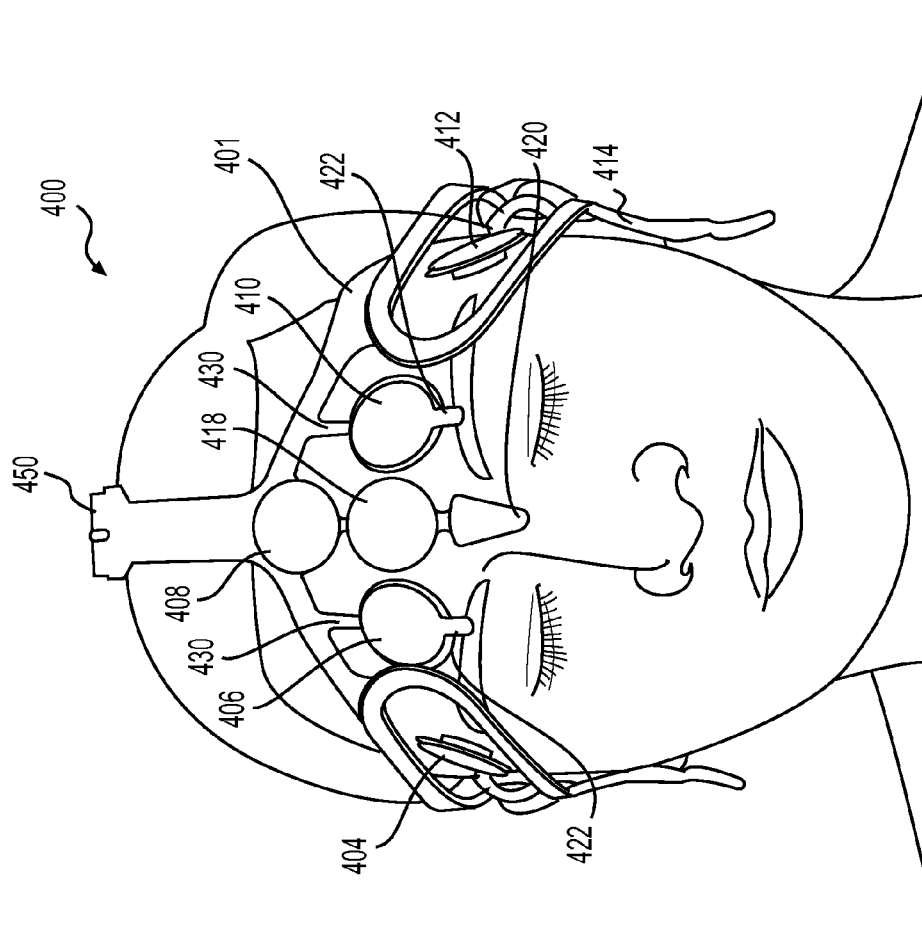
FIG. 4B depicts a front view of the exemplary array of FIG. 3 in a first position when fitted on a subject.
Figure 5:
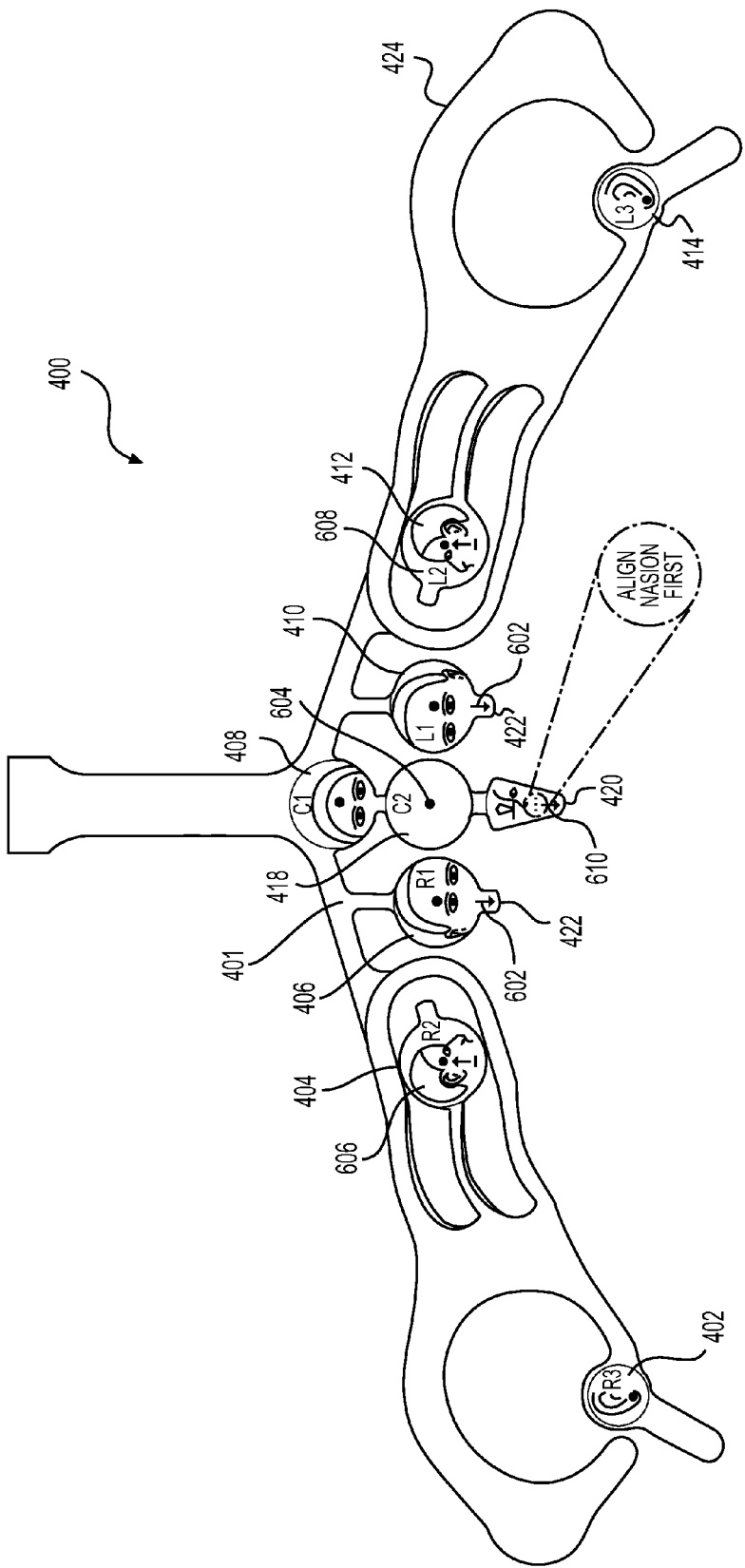
FIG. 5 depicts an exemplary array, in accordance with an embodiment of the present disclosure.

Array 400 may be applied to the forehead of a subject with ear loops 424 disposed around a subject's ears, as depicted in FIG. 4A, generally positioning array 400 across the subject's forehead and maintaining array 400 in place. Once array 400 is preliminarily in place, as is depicted in FIG. 4B, a nasion point 420 on headset 400 may be aligned with the subject's nasion region, located at the top of the nose in a depressed region directly between the subject's eyes. Positioning nasion point 420 so that the lower tip aligns with the patient's nasion may substantially align the front, center portion of array 400 on the subject. Next, the position of center electrode 408 may be checked and adjusted if necessary. If positioning the tip of nasion point 420 directly at the subject's nasion causes electrode 408 to fall within the subject's hairline, then electrode 408 and array 400 may be lowered on the subject's forehead so that electrode 408 is located just below the hairline. This allows electrode 408 to be positioned on the skin of the forehead rather than in the hair, reducing the interference that may be created by positioning the electrode over the hair. This may allow array 400 to be adjusted for the unique anatomical features of the subject. Positioning nasion point 420 and center electrode 408 may occur either before or after arranging ear loops 424 around the subject's ears. Once ear loops 424 are positioned over the ears, electrodes 402 and 414 may be attached to the subject's ear lobes.

Once electrode 408 is positioned, electrodes 406 and 410 may require adjusting. The position of electrodes 406 and 410 may be adjusted relative to the subject's supraorbital foramen, which is located above the eye socket where the subject's eyebrows are located. For the purpose of this application, the words 'eyebrow' and 'supraorbital foramen' may be used interchangeably. To allow the person applying array 400 to position electrodes 406 and 410 on a subject, array 400 may include one or more distance indication gauges. In FIG. 4A through FIG. 5, the depicted distance indication gauge includes tabs 422 extending down from electrodes 406 and 410. The distance from the bottom tips of tabs 422 to the center of electrodes 406 and 410 corresponds to the optimal predetermined distance between electrodes 406 and 410 and the top of the subject's eyebrows. Tabs 422 are positioned on the subject so that the bottom of tabs 422 sits above, preferably directly above, the peak of the subject's eyebrow so that the bottom of tabs 422 does not touch the subject's eyebrows. If the subject does not have any eyebrows, then the bottom of tabs 422 is positioned above the peak of the subject's supraorbital foramen, which lies in substantially the same location as the eyebrows.

Figure 6A:
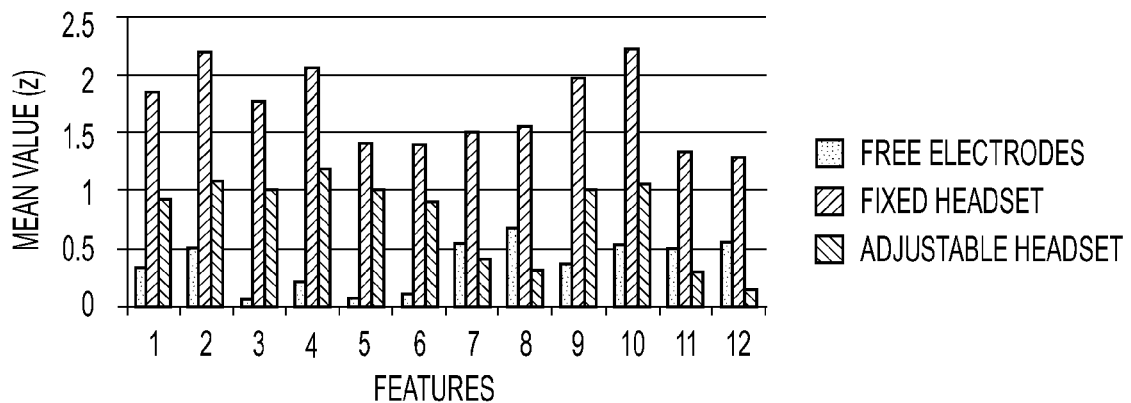
FIGS. 6A through 6C illustrate graphical comparisons of different features of different signal properties measured using free electrodes, a fixed headset, and an exemplary array according to an embodiment of the present disclosure.
Figure 6B:
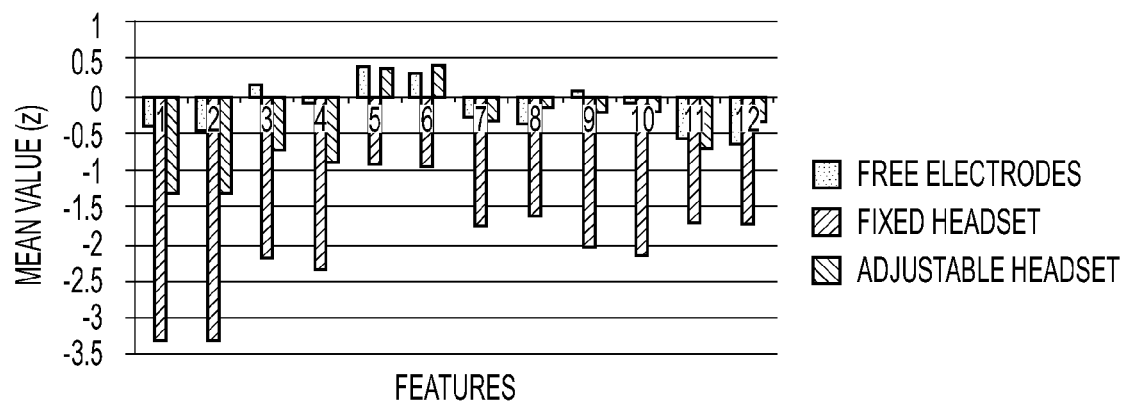
Figure 6C:
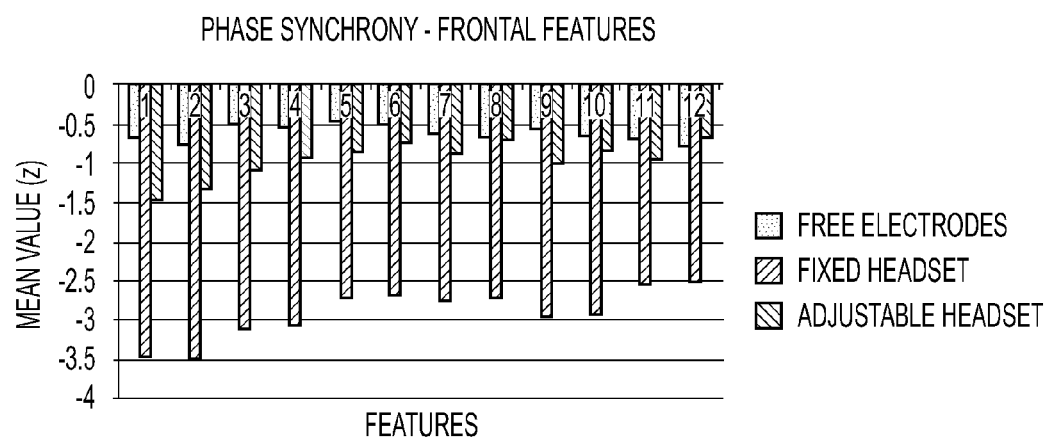

Positioning tabs 422 directly above the subject's eyebrows may locate electrodes 406 and 410 in an optimal location for recording usable EEG readings from the subject using array 400. Prior electrode arrays and headsets focused predominantly on the positioning of each electrode relative to each other and attempted to provide a way to maintain uniform positioning of the electrodes relative to each other for each subject. Accordingly, in such devices, electrodes 406, 410, and 408 had fixed, non-adjustable positions in the headset and were applied all together to a subject. Thus, the position of electrodes 406 and 410 relative to center electrode 408 could not be adjusted. While this fixed arrangement worked for some uses, as discussed above in reference to sedation-monitoring purposes, this fixed arrangement of electrodes 406, 410, and 408 unexpectedly provided inadequate EEG readings for discriminating between normal and abnormal electrical brain activity indicative of normal or abnormal brain function. For example, FIGS. 6A through 6C show data from experiments that measured and compared several exemplary properties of EEG signals recorded using free electrodes, a fixed headset, and an adjustable headset according to an exemplary embodiment of the disclosure. The graphs of FIGS. 6A through 6C depict 12 frontal features that were extracted from the EEG readings of normal subjects and the mean statistical z-score value of each feature calculated for all subjects tested in each of the free electrode, the fixed headset, and the adjustable headset groups. Thus, the mean z-scores of each feature are compared using the different EEG recording devices.

Features 1 through 12 shown in FIGS. 6A through 6C were achieved by calculating the bipolar absolute power for a pair of electrodes for each headset type within selected frequency bands, (a left and right feature across 6 frequency bands for a total of 12 features), and the phase symmetry and coherence relationships among these spectral measurements within and between pairs of electrodes. Measurements may be made between pairs of electrodes in a given headset in order to detect signal differences and to reject input signals common to both electrodes. This is because each electrode may acquire different brain activity, but noise influence may be similar on both electrode channels within the pair due to their close proximity on the subject's forehead. The computed measures were combined into a single measure of EEG signal per channel and transformed for Gaussianity, and a statistical z transformation was performed to produce z-scores. The z-transform was used to describe the deviations from normal EEG values.

The z-scores were calculated using a database of response signals from a large population of subjects believed to be normal. Thus, the z-scores were used to calculate the probability that the extracted feature observed in a subject conformed to a normal value. In the exemplary data of FIGS. 6A through 6C, a mean value of any feature for a "more normal" population would lie closer to the mean value for the normative population (i.e. mean=0, standard deviation=1) than the mean values of any feature in the "less normal" population. FIGS. 6A through 6C depict EEG measurements from normal subjects, thus the z-scores would be expected to lie closer to 0, with some normal variation. As the data shows, the mean z-score values for the fixed headset and the adjustable headset varied greatly, while the z-score values of the adjustable headset and the free electrodes more closely resembled each other and generally lie closer to a mean of 0. While the sample sizes for the fixed and adjustable headset groups were smaller than the sample size used for the free electrode group (which may explain why both of these groups displayed z-scores further from 0), the z-scores of the fixed headset group were noticeably different than the adjustable headset group across the exemplary set of features.

FIG. 6A compares features from bipolar absolute power measurements recorded with fixed and adjustable headset designs and free electrodes. Bipolar absolute power indicates the amount of energy being acquired by the electrodes. This property should be substantially consistent across the headset designs, as each headset should in theory be measuring similar brain electrical activity. FIG. 6A shows that the amount of energy detected by the fixed headset was substantially greater than that of free electrodes, which may imply that the fixed headset detected more than simply the EEG signal. Such noise may have been caused, e.g., by muscle activity due to placement of the electrodes near the eyebrows.

FIG. 6B compares features from coherence measurements recorded across the various electrode placement techniques. Coherence indicates the similarity of frequency content between the detected EEG signals. A more negative coherence value implies that the acquired EEG signal frequencies are less correlated, while a more positive value implies that detected signal frequencies detected are more correlated. Once again, across each feature, free electrodes and the adjustable headset displayed substantially similar coherence values, and, on average, these coherence values were noticeably different from those of the fixed headset. The more negative coherence values acquired by the fixed headset indicate that the detected signals are less correlated than they should be, which may again indicate signal contamination.

FIG. 6C compares features from phase synchrony measurements recorded with each electrode placement technique. Phase synchrony is similar to coherence, but includes measurement of the phase relationship between the pair of electrodes recorded. Thus, this feature analysis indicates that EEG recordings measured with the fixed headset were not only of a different frequency than expected, but also that these frequencies were not in phase. By contrast, recordings of the exemplary features taken with the free electrodes and the adjustable headset generally displayed more similar phase synchronies.

As the inventors' data illustrates, the EEG readings detected using array 400 are substantially different from those of fixed headsets, which marked a surprising discovery. It was previously believed that electrodes 406 and 410 should be located a set distance from center electrode 408. Thus, previous, fixed-headset devices reflected the concern that placing electrodes 406 and 410 too close to center electrode 408 would cause electrical shunting, increasing the noise and decreasing the amplitude of any detected EEG signals. Thus, previous headsets were designed to fix the distance between these electrodes, and the entire block of electrodes, as well as the grounding electrode, were applied in a predetermined, uniform position to a subject. Only the block of electrodes could be repositioned slightly on the subject; the electrodes could not be individually adjusted relative to each other. Yet, this approach produced EEG readings that did not accurately allow for detection of normal versus abnormal brain activity, as discussed above.

By contrast, as a result of much experimentation, the disclosed array shifts away from this fixed design and reflects the surprising discovery that achieving usable EEG readings involves a compromise between the proximity of electrodes 406 and 410 to electrode 408 and the proximity of electrodes 406 and 410 to the supraorbital foramen. Electrodes placed in the eyebrows of a subject may induce unwanted physiological effects on recorded EEG data, such as undesirable noise. The human face contains a number of muscles to control the movement of the eyes and eyebrows. Positioning electrodes 406 and 410 too close to the eyebrows may cause interference from the electrical activity of these muscles. By contrast, the forehead contains fewer muscles, and so positioning electrodes 406 and 410 away from the eyebrows by a set distance may result in clearer, more accurate, and more usable signals, as long as electrodes 406 and 410 are not placed too close to electrode 408.

After gathering much experimental data, it was discovered that there may be a calculable, average distance above a subject's eyebrows that may correlate to an optimum electrode position for generating signals usable to determine normal versus abnormal brain activity. When collecting and analyzing data, the preferred International 10/20 system location was used to determine 'ideal' placement of the Fp1 and Fp2 electrodes (electrodes 406 and 410 in array 400). The 10/20 electrode location is a subject-specific measurement that is determined based on the head size of each subject. Accordingly, the 'ideal' 10/20 location varies from subject-to-subject and must be calculated on an individual basis. To determine the average 'ideal' electrode placement across a population, head measurements were recorded from a group of subjects and averaged to calculate where the 10/20 location of the Fp1 and Fp2 electrodes should be relative to the average position of eyebrows and the average head size of the subjects.

Figure 7:
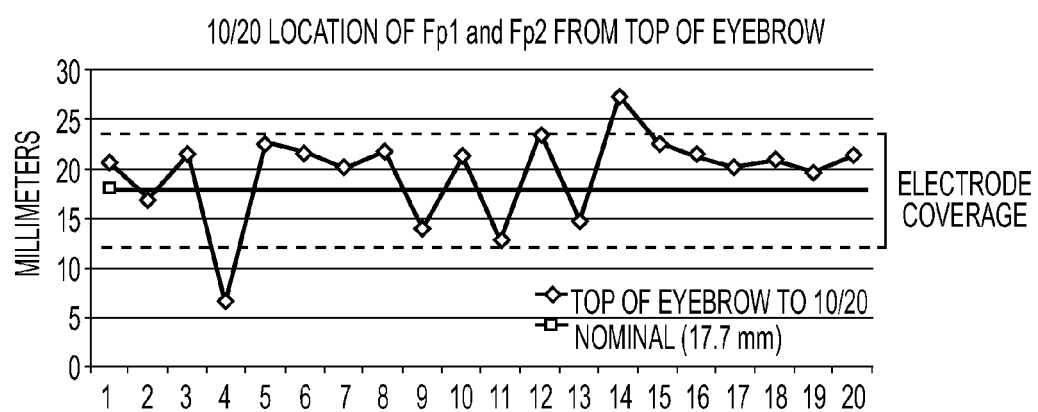
FIG. 7 illustrates a graphical representation of electrode location for an exemplary array according to an embodiment of the present disclosure.

FIG. 7 graphically depicts the relationship between the calculated 10/20 location of the Fp1 and Fp2 electrodes based on the measured nasion-to-inion distance in 20 subjects and the distance of this location from the top of a subject's eyebrows. As is demonstrated in FIG. 7, with the exception of a few outliers, the ideal electrode placement for Fp1 and Fp2 for most subjects tends to fall within an identifiable range, indicated in FIG. 7 by dashed lines. This range corresponds to between approximately 12 millimeters and 24 millimeters above a subject's eyebrow.

Array 400 may be configured to reflect the discovery that placing electrodes 406 and 410 a predetermined, consistent distance away from the subject's eyebrows may achieve an optimum placement for electrodes 406 and 410 to generate reliable EEG readings that are usable for determining levels of abnormal versus normal electrical brain function. For example, in some exemplary embodiments, the predetermined distance from the eyebrows to the center of electrodes 406 and 410 may equal approximately 17.7 millimeters. As is demonstrated by the solid line in FIG. 7, for the average person, centering the Fp1 and Fp2 electrodes 17.7 millimeters above the eyebrow may achieve the average optimal electrode placement across a population of subjects. In some embodiments, the predetermined distance used may vary, and the electrodes may be positioned slightly closer to or slightly farther from the eyebrow. As is demonstrated by the dotted lines in FIG. 7, positioning the Fp1 and Fp2 electrodes between approximately 12 millimeters and 24 millimeters may achieve an optimum placement. In addition, the electrodes may be sized so that when the center of the electrodes are placed 17.7 millimeters above the eyebrows, the size of the electrode itself spans a portion or substantially all of this range. Further, this range may change for given populations. For example, array 400 may be designed for youths and may position electrodes 406 and 410 closer to the eyebrows to reflect a smaller average head size. In some embodiments, array 400 may be designed for a population of professional athletes, e.g., football, soccer, or hockey players, and the electrodes may be positioned farther from the eyebrows to reflect a larger average head size. Accordingly, measurements from a specialized sub-population may be taken to create a specialized array 400. In some embodiments, the predetermined average distance may also vary depending on the configuration of array 400 used, including, e.g., the size of the electrodes or the configuration of substrate 401.

Once the predetermined distance is calculated, the distance indication gauge of array 400 may be formed to achieve this predetermined distance. Based on the size and location of the electrodes and the size and shape of substrate 401 depicted in the exemplary array 400 of FIGS. 3 through 5, the length of tabs 422 may be approximately 5 millimeters in length in order to position electrodes 406 and 410 a predetermined distance of approximately 17.7 millimeters away from a subject's eyebrows. One will appreciate that the length of tabs 422 may vary in order to achieve the predetermined distance depending on the placement of electrodes within array 400, the size and shape of substrate 401, or any other variations in configuration of array 400 and/or the calculated predetermined distance. For example, if substrate 401 extends further in a distal direction below electrodes 406 and 410, then tabs 422 may be shortened to achieve the same predetermined distance from the bottom of tabs 422 to the center of the electrodes.

As can be seen in FIGS. 3-5, electrodes 410 and 406 are not directly laterally tethered to electrode 408 and grounded electrode 418 by array 400, allowing the electrodes to be applied to a subject independently of one another. Decoupling electrodes 406, 410, and 408 may also have the benefit of reducing muscle-induced interaction that may otherwise occur between the electrodes. Yet, removing the fixed arrangement of electrodes once again decreases the likelihood that a lay person at the point-of-care would be able to effectively apply array 400 to the subject. Thus, array 400 may be configured to dictate to the user what adjustments should be made and how to accomplish them.

Figure 4C:
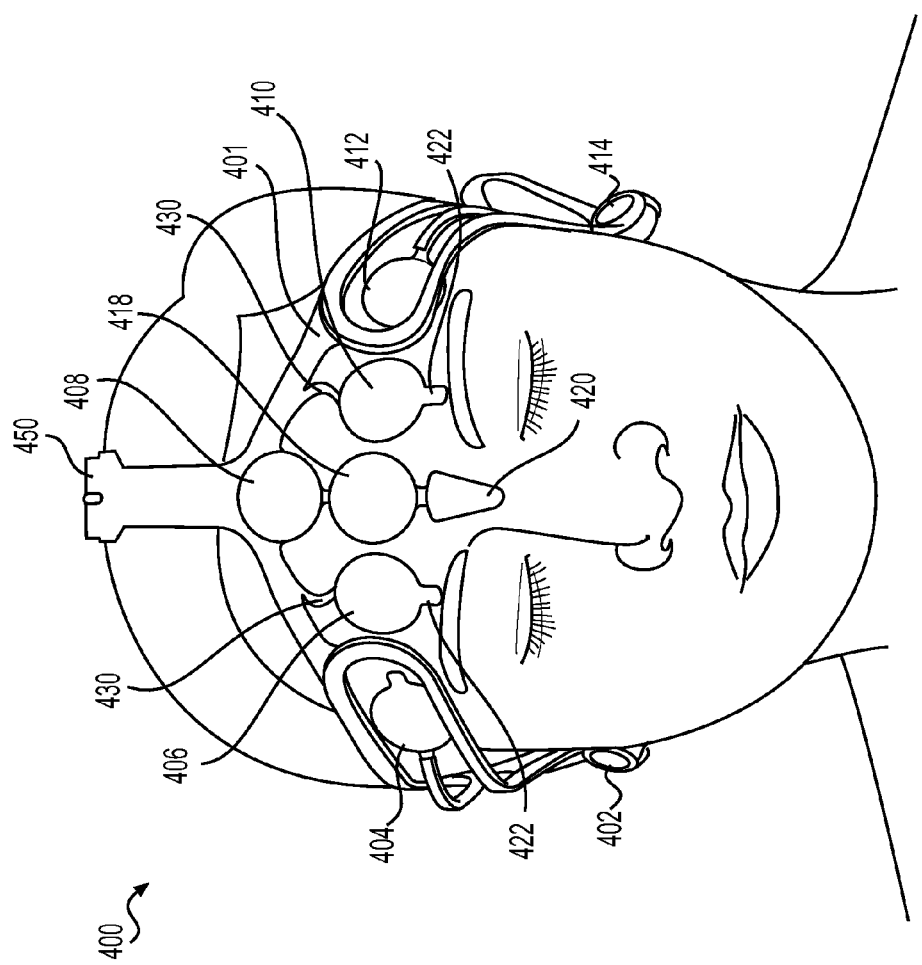
FIG. 4C depicts a front view of the exemplary array of FIG. 3 in a second position when fitted on a subject.

Incorporating tabs 422 into array 400 allows an untrained person to rapidly and accurately place electrodes 406 and 410 onto a subject properly for signal acquisition. Ready visual confirmation that tabs 422 do not rest at the top of the subject's eyebrows once electrode 408 is in place can be quickly remedied by manual adjustment of the placement of electrodes 406 and 410. As is shown in FIG. 4B, when array 400 is first placed on a subject, tabs 422 may extend beyond the top of the subject's eyebrows once electrode 408 is set in place below the subject's hair line. This suboptimal placement could compromise signal quality, and ultimately reliability of calculated results. FIG. 4C shows electrodes 406 and 410 adjusted so that the bottom of gauge tabs 422 are aligned in a prescribed way, which for the purposes of this example, is with the tip of the tabs 422 just above the eyebrow. Of course, other indicia of alignment may be employed without limitation.

As is shown in FIG. 4C, electrodes 406 and 410 may be connected to array 400 via connector regions 430. Connector regions 430 may be flexible and may allow electrodes 406 and 410 to be moved upwards towards electrode 408 so that connector regions 430 bow out, as is shown in FIG. 4C. In some embodiments, connector regions 430 may be retractable into the branching portions of array 400, or may be otherwise folded or configured to allow at least vertical movement of electrodes 406 and 410. Thus, a user may adjust the relative spacing of electrodes on array 400 by moving electrodes 406 and 410 so that the bottom of tabs 422 rest above the subject's eyebrows, as discussed above.

Incorporating distance indication gauges, such as tabs 422, into array 400 may promote consistent headset orientation and application while achieving the adaptability required to obtain usable EEG readings, based on the recognition by the present inventors of the relationship between signal quality and the distance between the supraorbital foramen and electrodes 406 and 410, and the further recognition that while relative electrode placement laterally can vary with facial morphology, this distance is substantially stable among subjects. While the exemplary embodiments depict distance indication gauges in the form of tabs 422, any suitable distance indication gauge, indicia, device, or combinations thereof may be included in array 400. For example, the portions of array 400 containing electrodes 406 and 410 could themselves be sized and shaped so that the distance between the bottom of the these portions and the electrodes reflects the ideal distance from the supraorbital foramen. In such embodiments, array 400 may not include tabs 422, and instead, the portions of array 400 around electrodes 406 and 410 may simply extend down to where the bottom of tabs 422 is shown in FIGS. 3-5. Thus, rather than aligning tabs 422, a user applying array 400 may simply adjust 406 and 410 so that the bottom of each rests directly above the eyebrow. In such embodiments, portions 406 and 410 containing the electrodes may be elongated, oval, rectangular, triangular, or any other suitable shape.

In some embodiments, a distance indication gauge for array 400 may include one or more sensors configured to detect when ideal electrode placement has been achieved. For example, the area of array 400 around electrodes 406 and 410 may include sensors to detect whether the electrode is positioned too close to the muscles underlying the eyebrow region. Such sensors may, e.g., emit a wavelength of light and measure one or more properties of a reflected light wavelength to determine whether the electrode is located too close to muscles to avoid the introduction of unwanted noise into subsequently recorded signals. Similar sensors may be included in other electrodes, e.g., 404 and 412, to indicate whether an electrode is being placed too close to an underlying artery, vein, or other anatomical structure. In some embodiments, electrodes 406 and 410 and base 42 may be configured so that if electrical brain activity outside of a given range is recorded, a user may be prompted to check the placement of these, or any other, electrodes. Such distance indication gauges are purely exemplary, and array 400 may include any suitable type of distance indication gauge for any indicating preferable placement of any electrode, or any combination thereof.

Once electrodes 406 and 410 have been positioned on the subject, electrodes 404 and 412 may be attached to the outer forehead region. Once array 400 is in place on the subject and each of the electrodes has been attached to the subject, array 400 may be operably coupled, either through a direct connection or wirelessly, to base 42, and EEG readings may be commenced. For example, in the embodiment depicted in FIG. 3, array 400 may include a base interface region 450 configured to couple with a suitable connection device attached to base 42.

Thus, a method of attaching array 400 to a subject may include positioning tab 420 at the nasion region of the subject to align electrodes 418 and 408, then adjusting the location of electrode 408 so that electrode 408 sits on the forehead directly below the hairline, and attaching electrodes 408 and 418 to the forehead. The method may further include engaging ear loops 424 with the ears of the subject so that array 400 is positioned across the forehead, and attaching electrodes 402 and 414 to the ear lobes of the subject. In some embodiments, these first two steps may be performed in reverse order, and electrodes 402 and 414 may be attached at any point during application. Next, electrodes 406 and 410 may be positioned by aligning tabs 422 directly above the eyebrows of the subject, so that the bottoms of tabs 422 do not touch the eyebrows of the subject. Electrodes 406 and 410 may then be attached to the subject. Electrodes 404 and 412 may then be attached to the forehead of the subject.

The electrodes of array 400 may be attached to the subject in any suitable manner. The electrodes included in array 400 may be any suitable type of electrode, e.g., wet gel or solid gel electrodes, or any combination thereof. The electrodes of array 400 may have backings or covers that may protect the electrode until being placed on the subject. A user may uncover the electrode prior to attaching the electrode to the subject. Any suitable backings may be used, such as removable, tear-able, or peel-able backings with or without an adhesive. In some embodiments, electrodes with, e.g., adhesive-free peel backings, may be used that allow for repositioning of the electrode on a subject. For example, a user applying headset 400 may accidently attach the electrode in the wrong place, such as accidently placing electrode 406 or 410 into, or at the wrong distance from, the eyebrow of a subject. This repositioning feature is desirable in urgent care or battlefield conditions, where placement of array 400 might take place in stressful or distracting situations. Additionally, an electrode site revealed as having a high impedance value when recording EEG signals may require the electrode to be removed, the skin re-prepped, and the electrode re-attached. In such instances, the user may need to adjust the placement of the electrode on the subject. In such an embodiment, tabs 422 may aid in repositioning. For example, a user may lift tab 422 to pull the corresponding electrode off of the subject's skin while allowing the user to avoid touching any adhesive, gel, or the electrode, so as to preserve usability of the electrode. In this manner, tabs 422 may serve a secondary function of aiding in the repositioning of electrodes on the subject, if necessary. This is another desirable feature in a battlefield or urgent-care setting, where the skin surface might be contaminated with dried blood, or the subject may exhibit individual features such as facial scarring, wrinkling, eczema, dermatitis, etc. Further, tabs 422 may also enable a user to more easily remove the electrodes and array 400 from the subject after completion of the EEG testing. To this end, other electrodes, such as electrodes 404 and 412, e.g., may include one or more tabs to achieve these secondary functions of repositioning and removal of the electrodes.

Accordingly, array 400 may be configured to allow multi-axis, independent control over the placement of individual electrodes. To further aid with the multi-axis adjustability of array 400, array 400 may also include visual indicia indicators on array 400 to instruct the user in proper alignment and use of array 400. For example, as is shown in FIG. 5, array 400 may include graphical indicators, text, or other symbols to indicate the preferred placement of array 400 on a subject. For example, nasion point 420 and tabs 422 may include arrows 610 and 602, or other suitable symbols, indicating where these components of array 400 may be positioned by the user. In some embodiments, portions of array 400 may include illustrations 606 pictorially demonstrating to a user where on the anatomy of a subject a given electrode may be placed. Further, indicators 604 may be included and may mark the position of the underlying electrode, e.g., the center or the edge of the electrode, to aid positioning. In the embodiment shown in FIG. 5, indicators 604 are used in combination with illustrations 606 to together demonstrate to a user where to place the underlying electrode on a subject. Further, textual indicators may be included on array 400. For example, in FIG. 5 nasion point 420 includes instructions to align the nasion point first, and electrodes 406, 410 may include text instructing a user to place tab 422 above the eyebrow. Additionally, textual indicators may warn to avoid other anatomical features, e.g., electrodes 404, 412, and 408 may warn a user to avoid placing the electrodes over an artery, muscles, or hair, for example. In some embodiments, one or more electrodes may include electrode labels to aid a user in distinguishing the electrodes from one another and for reference, e.g., in a set of instructions. In some embodiments, text or graphics may be incorporated that convey to the user the order in which electrodes should be placed or may include instructions for performing EEG recordings. Any suitable number, arrangement, or type of visual indicators may be included, including, e.g., color coding or shading. In some embodiments, visual indicators may change, for example, to signal to a user that an electrode is or is not correctly in place. In some embodiments, e.g., array 400 may include one or more lights that change color to indicate that a sensor is or is not correctly in place, e.g., by performing a preliminary impedance check. Further, any suitable non-visual indicators may be used, for example tactile (e.g., texture) or auditory indicators.

Referring back to FIG. 1, the memory 52 of brain-state assessment device 10 may contain interactive instructions for placing and adjusting array 400 and operating the device, which may be displayed, e.g., on the screen of user interface 46 or output from a speaker (not shown). Instructions may include, e.g., audio and/or visual instructions for operating the device, such as text or graphics displayed on the screen to illustrate instructions for placing and attaching array 400 and/or operating and using the device. These instructions may refer to one or more of the visual indications on array 400, if such indications are included. The inclusion of interactive instructions with the device may also promote point-of-care deployment and use of apparatus 10 by persons other than medical professionals.

In some embodiments, once array 400 has been applied to a subject and connected (either physically or wirelessly) to base unit 42, base unit 42 may be configured to aid a user in determining whether suitable placement of array 400 has been achieved. For example, base unit 42 may run a preliminary impedance check to determine whether array 400 is ready to begin recording and testing or whether additional modifications to array 400 on the subject are necessary. In some embodiments, once array 400 is positioned on the subject and connected to base unit 42, the user may employ user interface 46 to initiate a pre-test sequence, or a pre-test sequence may be initiated automatically. During a pre-test sequence, impedance may be automatically measured on each electrode channel, either simultaneously, individually, or in groups, by sending a small amplitude sinusoidal signal to the electrodes via grounded electrode 418. The resulting current, which is proportional to impedance, may then be measured for each electrode.

Base unit 42 may then output data regarding the status of each electrode to the user. For example, a display in base 42 may indicate the current and/or impedance value measured for each electrode and may indicate whether the measured value falls within an normal range for that electrode. This may be accomplished using visual output (e.g., text or graphics), auditory output, or a combination thereof. For example, a display in user interface 46 may depict a diagram of each electrode on the subject and the corresponding measured impedance value for each. The expected impedance range and/or whether an electrode falls in the expected range may also be depicted. These values may either be depicted using text or graphics or a combination. In some embodiments, the electrodes may be color-coded according to the measured impedance of each to indicate whether the recorded value is within an optimal range or not. For example, green may indicate that an electrode has a normal impedance value, yellow may indicate an acceptable impedance value, and orange may indicate an unacceptable impedance value. A normal impedance value may be identified as between approximately 0.5 and 5.0 k$\Omega$, an acceptable impedance value may be between approximately 5.0 and 10.0 k$\Omega$, and an unacceptable impedance value may be greater than approximately 10.0 k$\Omega$.

Based on this information, a user may adjust one or more electrodes before initiating testing. Tabs 422 may assist with the adjustment of one or more electrodes, as discussed above. Adjusting may include lifting the problem electrode, re-prepping the underlying area on a subject, and re-attaching the electrode. Once the electrodes are adjusted, this pre-check sequence may be performed again. Once normal and/or acceptable values are achieved for each electrode in array 400, testing may begin either automatically or via user input. In some embodiments, apparatus 10 may not allow testing to begin until base 42 detects that all of the electrodes have impedance values falling within a predetermined range.

In some exemplary embodiments, array 400 may be applied to a subject, base 42 may be powered on, and a user may indicate that a new test will be performed. At this step, patient information (such as date of birth, name, patient ID number, sex, age, physiological parameters, etc.) or array 400 information (such as model number, lot number, calibration information, etc.) may be entered using user interface 46. At this point, an impedance pre-check screen may be selected or may automatically appear, and an impedance check as described above may be initiated.

In some embodiments, placement of array 400 on a subject and connection of array 400 to base 42 may initiate other communications between array 400 and base 42, instead of, or in addition to, an impedance check. For example, connecting array 400 may prompt base 42 to power on or may cause base 42 to receive and/or relay information about array 400, e.g., its expiration date, model number, lot number, calibration information, the number of times array 400 has been used, or any other suitable information or combination of information. Such information may promote proper use of and/or accurate readings from system 10.

Array 400 may be disposable or reusable. In some embodiments, the electrodes of array 400 may be mounted on a low-cost, disposable platform. Array 400 may be formed of any suitable flexible or rigid materials, including, e.g., plastic, foam, rubber, silicone, or any combination thereof. In some embodiments, array 400 may be formed of multiple layers, for example, portions of array 400 may include reinforcement layers to provide structural stability, dielectric layers, or adhesive layers for maintaining array 400 on a subject. For example, ear loops 424 may include an additional layer of foam or padding for stability or to increase subject comfort. Ear loops 424 may also include a malleable, internal layer or wire to allow an operator to bend the ear loops around a subject's ears, providing improved anchoring of array 400 on a wider range of head shapes and sizes. Further, any circuitry on array 400 may be covered by a dielectric layer to help insulate or protect the circuitry, which may be formed of, e.g., polyamide, polyester, aramid, or any dielectric or combination thereof. Such layers may extend across the entire array 400 or may extend across only a portion of array 400. In multi-layer embodiments, the layers of array 400 may be attached in any suitable manner, e.g., bonding, adhesives, mechanical fasteners, or any combination thereof.

In some embodiments, array 400 may be configured to adjust to any number of subject head sizes or geometries. For example, array 400 may include adjustable bands, straps or loops, or may stretch or include any suitable mechanism for conforming to a range of subject head sizes and anatomical variations. In some embodiments, array 400 may include one or more expansible regions, for example, outward-bowing humps or accordion-shaped articulation ridges, capable of flattening to expand or contracting to adjust to a subject's head shape and/or size. Such regions may include flexures, elastics, corrugations, serpentine geometries, or any other suitable construction to allow variation in overall size, e.g., height or length, of array 400. For example, securing ear loops 424 to the ears of a subject and positioning array 400 across the forehead may cause any expansible regions to stretch or contract to accommodate the head geometry and size of the subject. Additionally, by permitting independent placement of the electrodes, array 400 may further be able to accommodate an increased range of subject sizes and anatomies. Further, array 400 may also come in different sizes, e.g., for youths or adults. In some embodiments, array 400 may be configured for easy and/or rapid placement on a subject.

Surprisingly, when testing prior headset designs, it was discovered that the bulk and design of the array itself may also affect EEG readings, beyond just determining or influencing the spacing and arrangement of electrodes. For example, when free electrodes were applied to a subject and then the space between the electrodes on the subject's skin was filled in and covered with an inert material (e.g., tape, paper, or foam), the EEG readings received from the headset in some instances were less useful for discriminating between levels of normal and abnormal brain activity for diagnosing disease or injury and more closely resembled the readings from the fixed headset designs. Without being bound by theory, the present inventors speculate that this phenomenon may be because the placement of more material into contact with a subject's forehead may induce electrical activity, for example, by muscular twitching or by the activation of sensory neurons responsive to touch. This electrical activity in turn may introduce noise into the EEG signals. Accordingly, some embodiments of the present disclosure may include arrays 400 that are configured to reduce the amount of material in contact with the subject, as well as to allow for adjustability of electrodes. For example, portions of array 400 may be streamlined or have geometries configured to decrease contact between array 400 and the subject. For example, portions of array 400 that are configured to flex or extend to fit various head sizes or to allow for adjustment of individual electrodes may be configured to bow away from the subject when flexed, so as to decrease contact between the subject and the headset. Decreased contact and/or streamlined configurations may have the added benefit of allowing a user placing array 400 on a subject to see more of the subject's forehead when placing array 400 on the subject and when adjusting and attaching electrodes 406 and 410, which may promote quick application of array 400. Thus, different embodiments of the disclosure may be configured to offer different degrees of contact between array 400 and the subject and may have different widths, for example, of the branching portions of array 400 or connector regions 430.

Referring back to FIG. 1, the electrodes in array 400 may be configured to measure the electrical fields that are produced as a result of a subject's electrical brain activity. The activity may be spontaneous, evoked or a combination thereof. In some embodiments, spontaneous brain activity may be measured while a subject is at rest or while the subject's eyes are closed, to reduce the number of stimuli the subject is exposed to during the testing (i.e., remove visual stimuli). In some embodiments, both spontaneous and evoked responses may be measured. The evoked response may be obtained by stimulating the subject using visual, physical, aural or other suitable stimulation. In such an embodiment, one or more stimuli may be delivered to the subject via a stimulus delivery device 31, which may be separate from or incorporated into array 400. Stimuli generator 54 in base 42 may relay a signal to stimulus delivery device 31, initiating the delivery of one or more stimuli to a subject to obtain an Auditory Evoked Response (AEP). In some embodiments, array 400 may also include sensors in addition to the electrodes discussed above, for example, to measure the heart rate, temperature, blood pressure, or other suitable physiological parameters of the patient to relay to base 42. Such additional information may be monitored, either continuously or intermittently, and/or used in addition to the EEG readings to assess brain function and subject condition.

Functional brain state assessment may be made by recording and analyzing electrical brain activity of subjects with suspected neurological injury. A handheld, easy-to-administer brain wave assessment device may facilitate neurological evaluation of subjects at the point-of-care, which in turn may allow rapid and accurate initiation of therapy. Once array 400 is applied to a subject, a subject's brain electrical impulses detected by the electrodes may be transmitted to base unit 42 and/or an external processor 48 for signal analysis and data processing. Additionally, these components may perform other steps, including signal amplification, artifact rejection, signal extraction, and classification of signal features. Base 42 and/or external devices may process EEG data using any combination of signal processing methods, algorithms, and statistical analysis to extract and/or organize signal features, including, e.g., Fast Fourier Transform (FFT) analysis, wavelet analysis, Linear Discriminant Analysis, spectral analysis, microstate analysis, fractal mathematics, nonlinear signal processing, and diffusion geometric analysis, to analyze and classify electrical brain activity.

Advanced signal processing algorithms may be used in conjunction with a database of pre-recorded brain activity received from thousands of subjects having different neurological indications to assess the neurological function of a subject, e.g., whether it falls within normal or abnormal ranges, or varying degrees thereof. The dysfunctions detected may include, for example, seizure, ischemic stroke, elevated intracranial pressure, hematoma, concussion/contusion/TBI, dementia, and depression. The results of such analysis may be displayed to a user on user interface 46 or communicated to a user in any suitable manner, or transmitted to or recorded by any suitable end point, e.g., a memory, printer, or emergency response team. Exemplary systems for point-of-care neuro-assessment are disclosed in commonly assigned U.S. Publication Nos. 2011/0144520 and 2012/0065536 and U.S. Pat. Nos. 8,364,254; 7,904,144; 7,720,530, which are each incorporated herein by reference in their entirety. Accordingly, the disclosed electrode array may be used in conjunction with a portable handheld device for rapid, point-of-care, neurological evaluation to determine an appropriate course of treatment at an early stage of injury, or other brain disorder requiring medical attention.

Other embodiments of the disclosure will be apparent to those skilled in the art from consideration of the specification and practice of the disclosure herein. It is intended that the specification and examples be considered as exemplary only, with a true scope and spirit of the invention being indicated by the following claims.

What is claimed is:

1. A headset for detecting brain electrical activity of a human subject comprising:
   a flexible substrate dimensioned to fit a forehead of the subject having a first end and a second end, wherein the first end and the second end each includes a securing device configured to engage an ear of the subject to position the substrate across the forehead, and wherein the substrate includes at least one expansible region permitting a distance between the first end and the second end to selectably vary;
   a plurality of electrodes disposed on the substrate so that the electrodes contact the subject when the headset is positioned on the subject;
      wherein a first electrode is configured to contact a top center region of the forehead, a second electrode is configured to contact a lower center region of the forehead, a third electrode is configured to contact a front right region of the forehead, a fourth electrode is configured to contact a front left region of the forehead, a fifth electrode is configured to contact a right side region of the forehead, and a sixth electrode is configured to contact a left side region of the forehead;
      wherein one electrode is included within each securing device and configured to contact an ear region of the subject when the headset is positioned on the subject, and
      wherein at least the third electrode and the fourth electrode are movable in at least a vertical direction relative to the other electrodes when the headset is positioned on the subject; and
   flexible circuitry in the substrate operably coupled to each electrode.

2. The headset of claim 1, wherein at least one of the plurality of electrodes is a grounded electrode.

3. The headset of claim 1, wherein at least the third electrode and the fourth electrode each includes a distance indication gauge.

4. The headset of claim 3, wherein the distance indication gauge includes a tab with a first end connected to the electrode and a second free end extending from the electrode.

5. The headset of claim 4, wherein a distance from the second end of the distance indication gauge to a center of the electrode substantially equals a distance that the electrode is located from an anatomical feature of the subject when the headset is positioned on the forehead of the subject.

6. The headset of claim 5, wherein the anatomical feature is an eyebrow.

7. The headset of claim 5, wherein the distance from the second end of the distance indication gauge to the center of the electrode is substantially equal to 17.7 millimeters.

8. The headset of claim 1, wherein the at least one expansible region includes a flexure in the substrate.

9. A headset for detecting brain electrical activity comprising:
- a flexible substrate dimensioned to fit a forehead of a human subject having a first end and a second end, wherein the first end and the second end each includes a securing device configured to engage an ear of the subject to position the flexible substrate across the forehead;
- a first sensor disposed on the flexible substrate and configured to contact an upper center region of the forehead when the headset is positioned on the subject;
- a second sensor disposed on the flexible substrate and configured to contact a lower center region of the forehead when the headset is positioned on the subject;
- a third sensor disposed on the flexible substrate and configured to contact a left frontal region of the forehead when the headset is positioned on the subject, wherein the headset is adjustable such that the position of the third sensor is movable relative to the position of the first sensor;
- a fourth sensor disposed on the flexible substrate and configured to contact a right frontal region of the forehead when the headset is positioned on the subject, wherein the headset is adjustable such that the position of the fourth sensor is movable relative to the position of the first sensor;
- a fifth sensor disposed on the flexible substrate and configured to contact a left side region of the forehead when the headset is positioned on the subject;
- a sixth sensor disposed on the flexible substrate and configured to contact a right side region of the forehead when the headset is positioned on the subject;
- a seventh sensor disposed on the first end of the flexible substrate and configured to contact a left ear region of the subject when the headset is positioned on the subject; and
- an eighth sensor disposed on the second end of the flexible substrate and configured to contact a right ear region of the subject when the headset is positioned on the subject,
- wherein the second sensor, the third sensor, and the fourth sensor each includes an elongated portion having a first end connected to the sensor and a free end extending from the sensor.

10. A method of applying the headset of claim 9, the method comprising:
- positioning the free end of the elongated portion of the second sensor at a nasion region of the subject to align the second sensor and the first sensor on the forehead;
- adjusting the location of the first sensor so that the first sensor is located on the forehead below a hairline of the subject;
- attaching the first sensor and the second sensor to the forehead of the subject;
- engaging the first end with a first ear region of the subject;
- engaging the second end with a second ear region of the subject;
- attaching the seventh sensor to the first ear region and attaching the eighth sensor to the second ear region;
- positioning the free end of the elongated portion of the third sensor directly above a first eyebrow of the subject so that the free end does not touch the first eyebrow and attaching the third sensor to the forehead of the subject;
- positioning the free end of the elongated portion of the fourth sensor directly above a second eyebrow of the subject so that the free end does not touch the second eyebrow and attaching the fourth sensor to the forehead of the subject;
- attaching the fifth sensor to the forehead of the subject; and
- attaching the sixth sensor to the forehead of the subject.

* * * * *